United States Patent
Alt et al.

(10) Patent No.: US 10,760,059 B1
(45) Date of Patent: Sep. 1, 2020

(54) REPROGRAMMED BETA CELLS FROM ADULT STEM CELLS

(71) Applicant: InGeneron, Inc, Houston, TX (US)

(72) Inventors: Eckhard U. Alt, Houston, TX (US); Tahereh Karimi, Houston, TX (US)

(73) Assignee: InGeneron Inc., Houston, TX (US)

( * ) Notice: Subject to any disclaimer, the term of this patent is extended or adjusted under 35 U.S.C. 154(b) by 83 days.

(21) Appl. No.: 15/590,814

(22) Filed: May 9, 2017

Related U.S. Application Data

(60) Provisional application No. 62/333,845, filed on May 10, 2016.

(51) Int. Cl.
| | |
|---|---|
| *C12N 5/071* | (2010.01) |
| *A61K 35/39* | (2015.01) |
| *A61K 9/00* | (2006.01) |
| *A61L 27/38* | (2006.01) |

(52) U.S. Cl.
CPC .......... *C12N 5/0676* (2013.01); *A61K 9/0012* (2013.01); *A61K 35/39* (2013.01); *A61L 27/3804* (2013.01); *A61L 27/3839* (2013.01); *A61L 2300/43* (2013.01); *C12N 2501/50* (2013.01); *C12N 2501/60* (2013.01); *C12N 2506/1384* (2013.01); *C12N 2510/00* (2013.01)

(58) Field of Classification Search
CPC .............. C12N 2510/00; C12N 5/0676; C12N 2501/115; C12N 2501/999; C12N 2506/02; C12N 2506/22; C12N 15/85; C12N 15/86; C12N 2500/22; C12N 2501/06; C12N 2501/065; C12N 2501/105; C12N 2501/119; C12N 2501/15; C12N 2501/392; C12N 2501/40; C12N 2501/415; C12N 2501/60; C12N 2501/603; C12N 2501/604; C12N 2501/72; C12N 2501/727; C12N 2501/73; C12N 2506/1384; C12N 2710/10032; C12N 2710/10043; C12N 5/0619; A61K 35/39; A61K 35/12; A61K 35/35; A61K 35/51; A61K 35/545; A61K 38/00; A61K 48/00; C07K 14/70567; C07K 14/721; G01N 2500/10; G01N 33/5044
USPC .................................. 424/93.7; 435/377, 375
See application file for complete search history.

(56) References Cited

U.S. PATENT DOCUMENTS

2011/0280842 A1* 11/2011 Melton ................ C12N 5/0676
424/93.7

OTHER PUBLICATIONS

Pandian et al. Clinical and Translational Medicine 2014, 3:6, pp. 1-12 (Year: 2014).*

Akinci, E., et al. "Reprogramming of pancreatic exocrine cells towards a beta (β) cell character using Pdx1, Ngn3 and MafA," Biochemical Journal, 442(3): 539-550 (2013).
Ameri, J. et al., "FGF-2 Specifies hESC-Derived Definitive Endoderm Into Forgut/Midgut Cell Lineages in a Concentration Dependent Manner," Stem Cells 28, 45-56 (2010).
Arda, H.E, et al., "Gene Regulatory Networks Governing Pancreas Development," Developmental Cell 25, 5-13 (2013).
Bai et al., "Tracking Long Term Survival of Intramyocardially Delivered Human Adipose Tissue Derived Stem Cells Using Bioluminescence Imaging," Mol Imaging Biol. 13 (4), 633-45 (2011).
Benitez, CM., et al., "Deconstructing pancreas developmental biology," Perspect Biol. 4, 1-17 (2012).
Cheng, X., et al., "Self Renewing Endodermal Progenitor Lines Generated From Human Pluripotent Stem Cells," Cell Stem Cell 10, 371-384 (2012).
Donath M.Y., et al., "Mechanisms of β-Cell Death in Type 2 Diabetes," Diabetes 54(s2): S108-S113 (2005).
Francis M.P., et al., "Isolating adipose-derived mesenchymal stem cells from lipoaspirate blood and saline fraction," Organogenesis 6(1): 11-14 (2010).
Gefen-Halevi, S., et al., "Nkx 6.1 Promotes PDX1 Induced Liver to Pancreatic B-Cells Programming," Cellular Reprogramming 12 (6), 655-664 (2010).
Gittes, G.K., "Developmental Biology of the Pancreas: A comprehensive review," Developmental Biology 326, 4-35 (2009).
Greggio, C., "Artificial three-dimensional niches deconstruct pancreas development in vitro," Development 140 (121), 4452-4462 (2013).
Hebrok, M., "Hedgehog signaling in pancreas development", Mech. Dev. 120 (1), 45-57 (2003).
Islas, J.F. et al., "Transcription factors ETS2 and MESP1 transdifferentiate human dermal fibroblasts into cardiac progenitors," Proc. Natl. Acad. Sci. 109 (32), 13016-21 (2012).
Kroon, E., et al., "Pancreatic endoderm derived from human embryonic stem cells generates glucose-responsive insulin secreting cells in vivo." Nat. Biotechnol. 26, 443-452 (2008).
Lima M.J., et al., "Generation of Functional Beta-Like Cells from Human Exocrine Pancreas," PLoS One 11(5): e0156204 (2016).
Millman, J.R., et al., "Generation of stem cell-derived b-cells from patients with type 1 diabetes," Nature Communications 7:11463 (2016).
Oh K., et al., "In Vivo Differentiation of Therapeutic Insulin-Producing Cells from Bone Marrow Cells via Extracellular Vesicle-Mimetic Nanovesicles," ACS Nano 9(12):11718-27 (2015).

(Continued)

*Primary Examiner* — Janet L Epps-Smith
(74) *Attorney, Agent, or Firm* — Boulware & Valoir

(57) ABSTRACT

Methods of differentiating unmodified adult stem cells into functional beta-like cells are provided, as well as compositions, tissues and devices containing such cells. The method requires inducing sequential expression of PDX1, NGN3, and MAFA in these stem cells to form reprogrammed beta cells. Methods of treating diabetes are also provided, comprising obtaining stem cells, preferably from a patient with diabetes, inducing sequential expression of PDX1, NGN3, and MAFA, in said stem cells to form reprogrammed beta cells, and introducing said reprogrammed beta cells into a pancreas of said patient. Alternatively, it may be possible to inject such cells systemically, if the cells are targeted for the pancreas. In yet another embodiment, the reprogrammed beta cells are placed into an artificial pancreas that is surgically placed or injected into the patient.

16 Claims, 5 Drawing Sheets

Specification includes a Sequence Listing.

(56) References Cited

OTHER PUBLICATIONS

Schaffer, A.E., et al., "Nkx 6.1 controls a gene regulatory network required for establishing and maintaining pancreatic Beta cell identity," Plos Genetics 9 (1), 1-15 (2013).
Wankhade, U.D., et al., "Advances in Adipose-Derived Stem Cells Isolation, Characterization, and Application in Regenerative Tissue Engineering," Stem Cells Int., 2016: 3206807 (2016).
Xu, H., et al., "The combined expression of Pdx1 and MafA with either Ngn3 or NeuroD improves the differentiation efficiency of mouse embryonic stem cells into insulin-producing cells," Cell Transplant. 22(1):147-58 (2013).

* cited by examiner

REPROGRAMMED BETA CELLS FROM ADULT STEM CELLS

PRIOR RELATED APPLICATIONS

This application claims priority to U.S. Ser. No. 62/333,845, titled INDUCED BETA CELLS FROM ADULT STEM CELLS, filed May 10, 2016. It is incorporated by reference herein in its entirety for all purposes.

FEDERALLY SPONSORED RESEARCH STATEMENT

Not applicable.

FIELD OF THE DISCLOSURE

This invention relates to methods for the production of reprogrammed or induced beta cells for use in the treatment of diabetes, as well as the reprogrammed or induced beta cells thereby produced and uses for same.

BACKGROUND OF THE DISCLOSURE

Beta cells (βcells) are a type of cell found in the pancreatic islets of the pancreas. They make up 65-80% of the cells in the islets. The primary function of a beta cell is to store and release insulin—a hormone that reduces blood glucose concentration. Beta cells can respond quickly to spikes in blood glucose concentrations by secreting some of their stored insulin, while simultaneously producing more.

Insulin release is mediated by ion channels. Voltage-gated calcium channels and ATP-sensitive potassium ion channels are embedded in the cell surface membrane of beta cells. These ATP-sensitive potassium ion channels are normally open and the calcium ion channels are normally closed. Potassium ions diffuse out of the cell, down their concentration gradient, making the inside of the cell more negative with respect to the outside (as potassium ions carry a positive charge). At rest, this creates a potential difference across the cell surface membrane of −70 mV.

When the glucose concentration outside the cell is high, glucose molecules move into the cell by facilitated diffusion, down their concentration gradient through the GLUT2 transporter. Since beta cells use glucokinase to catalyze the first step of glycolysis, metabolism only occurs around physiological blood glucose levels and above. Metabolism of the glucose produces ATP, which increases the ATP to ADP ratio.

The ATP-sensitive potassium ion channels close when this ratio rises. This means that potassium ions can no longer diffuse out of the cell. As a result, the potential difference across the membrane becomes more positive (as potassium ions accumulate inside the cell). This change in potential difference opens the voltage-gated calcium channels, which allows calcium ions from outside the cell to diffuse into the cell, down their concentration gradient. When the calcium ions enter the cell, they cause vesicles containing insulin to move to, and fuse with, the cell surface membrane, releasing insulin by exocytosis.

Diabetes mellitus is a disease caused by the loss or dysfunction of insulin-producing beta cells in the pancreas. Specifically, in type 2 diabetes mellitus, beta cells exhibit an impaired capacity to compensate for increased insulin demand, a defect that has been ascribed to both inadequate cellular capacity to secrete insulin and beta cell death. In addition, diabetes can be accompanied by peripheral insulin resistance.

This impairment in glucose-stimulated insulin secretion has been attributed to defects in glucose sensing, mitochondrial dysfunction and oxidative stress. Results of other studies suggest that defects in multiple cellular processes can compromise beta cells function and can be a factor to induce diabetes mellitus. A simultaneous loss of beta cell function and identity could be explained by reduced expression of a central transcriptional regulatory network involved in beta-cells differentiation and maintenance. Recent studies suggest that dysregulation of the beta cells' differentiation state is among the earliest events marking the progressive failure of beta cells in diabetes (FIG. 1).

Therefore, innovative strategies for diabetes therapy aim to replace lost or damaged insulin-producing beta cells by reprogramming of other cell types towards beta cells lineage. Previous studies concentrated on the reprogramming of embryonic pluripotent or induced pluripotent stem cells towards beta cells using various factors (FIG. 2) (Kroon, 2008; Greggio, 2013). These differentiated cells, however, often lack much of the structure and markers that beta cells need to perform their necessary functions. Examples of the anomalies that arise from beta-like cells differentiated from progenitor cells include a failure to react to environments with high glucose concentrations, an inability to produce necessary beta cell markers, and abnormal expression of glucagon along with insulin.

Efficient and reproducible differentiation of initially unmodified autologous adult stem cells into glucose-responsive, insulin-producing beta cells has not been done. Most of the previous studies for production of beta cells have been based on the attempts to up-regulate one or two insulin inducing factors and had only marginal success.

Therefore, what is still needed in the art are robust methods for generation of pancreatic beta-cells by genetic re-programming of primary unmodified adult adipose derived stem cells (ADSCs) or other adult stem cells.

SUMMARY OF THE DISCLOSURE

In this work, adult adipose derived stem cells (ADSCs) were reprogrammed towards beta cell lineages by different combinations of transcription factors including PDX1, NGN3 and MAFA that were sequentially applied to the cells.

PDX1 (pancreatic and duodenal homeobox 1), also known as insulin promoter factor 1, is a transcription factor necessary for pancreatic development, including β-cell maturation, and duodenal differentiation. In humans, this protein is encoded by the PDX1 gene, which was formerly known as IPF1.

NGN3, or Neurogenin 3, is another member of the bHLH family of transcription factors. NGN3 functions in the differentiation of endocrine pancreas cells. Although its key function is in the pancreas, intestinal cells and neural cells express NGN3 as well. Several studies have highlighted the importance of NGN3 for differentiation of endocrine cells. In mice, NGN3 is present in cells as the pancreas begins to bud and glucagon cells are formed. There are several pathways that NGN3 works through. NGN3 is a crucial component in pancreatic development and plays a supporting role in intestinal as well as neuronal cell development. Studies have demonstrated that knockout of NBN3 in mice leads to death shortly after birth possibly due to after-effects of severe diabetes.

MAFA is a transcription factor that binds RIPE3b, a conserved enhancer element that regulates pancreatic beta cell-specific expression of the insulin gene.

NKX6.1 or NKX6-1 aka NK HOMEOBOX, FAMILY 6, and MEMBER A. In the pancreas, NKX6.1 is required for the development of beta cells and is a potent bifunctional transcription regulator that binds to AT-rich sequences within the promoter region of target genes.

Generally speaking, we used adipose tissue derived stem cells transfected or transduced in a defined sequence with expression vectors encoding PDX1, NGN3 and MAFA such that each of the genes was sequentially transcribed, leading to sequential production of functional proteins. However, the adult adipose derived stem cells are exemplary only and suitable pluripotent adult stem cells recovered from other sources can be used as well.

In our experience, the proteins needed to be sequentially introduced into the cell in a particular sequence order and amount (FIG. 3). Attempting to express all genes at once or not keeping the correct sequence of expression can lead to unsatisfactory results, thus in proof of concept work, we performed sequential transductions. However, a single vector encoding all genes under sequential inducible expression promoters is another approach to sequential activation, and the single transfection or transduction is less stressful for the cells. We have performed both methods herein. Either way, the order of appearance of the proteins is important, as is the level of protein expression.

The vectors used herein were lentiviral vectors. However, this was exemplary only and any expression vector could be used. Alternatively, RNA or circular RNA could be used or even intact functional proteins.

DNA, RNA and protein can be introduced into the cells in a variety of ways, including e.g., microinjection, electroporation, and lipid-mediated transfection. RNA can also be deliver to cells using e.g., tat fusion using e.g., the HIV-1-tat protein. Tat has also been used for protein delivery. For example, a tetramethylrhodamine-labeled dimer of the cell-penetrating peptide TAT, dfTAT, penetrates live cells by escaping from endosomes with high efficiency. Other cell-penetrating peptides (CPPs) are also known, and indeed intact proteins can be delivered using CPPs as fusion proteins, as well as by noncovalent CPP/protein complexes.

At the current time, retroviruses are preferred for gene therapies (retroviral and lentiviral) and have now been used in more than 350 gene-therapy studies. Retroviral vectors are particularly suited for gene-correction of cells due to long-term and stable expression of the transferred transgene(s), and also because little effort is required for their cloning and production. However, it is anticipated that next generation vectors will continue to be developed.

Furthermore, with the advent of genome engineering techniques (such as CRISP/CAS (and the like), it is also possible to selectively activate the needed proteins via genome engineering, rather than by cell delivery of DNA, RNA, or protein. Selective epigenetic changes (e.g., changing methylation patterns) may also be possible in the future.

While a number of different multipotent or pluripotent stem cell types could be used herein, the main value of the invention lies in treating diabetes in humans. Therefore, the preferred source of stem cells are autologous cells, such as e.g., adult adipose tissue derived stem cells. In the future, when umbilical tissue derived stem cells are stored from larger number of donors, e.g., cord blood and umbilical tissue derived stem cells and the like, other types of stem cells in a matched allogenic transplant manner may be preferred, but at the current time, these resources are available for few patients.

No one to this point has used adult derived stem cells for the re-creation of beta cells. Such methods are a tremendous advantage over embryonic stem cells because they can be autologous, eliminating rejection problems, and are readily available, unlike embryonic stem cells. Furthermore, induced stem cells (so-called iPS cells who have de-differentiated to a more stem-like state) may not be safe, as at least one researcher has opined that such cells are very close to cancer cells and our own research confirms this. Adipose tissue is easily accessed with a modicum of discomfort, and many patients have significant amounts of such tissue available for use. Thus, this source is safer and conveniently available in large amounts.

Allogenic cells may also be suitable, although anti-rejection drugs are typically required if the HLA patterns do not match. However, such cells are in use today, and may be more amenable to use in the future as more and more banks collect and store cord blood, cord tissue, etc. and the stem cells generated thereby, particularly where libraries of hundreds and thousands of different HLA patterns can be collected and cryopreserved, so that the probability of a fully matched allogeneic transplant increases.

Alternatively, a library of reprogrammed beta cells can be generated in advance, so at the time of need, these cells will be readily available for transplantation. One interesting aspect is that in a matched allogic transplant of reprogrammed beta cells—despite a full 6 out of 6 match of HLA surface markers—the specific donor cell associated underlying genetics might be different from the recipients genetic pre-disposition to acquire Type 1 Diabetes and therefor the newly generated islet cells from a matched allogenic donor cell sample might not be prone to the autoimmune attack typically present against the host's own beta cells.

In addition, we have described the invention using human or mouse wild type genes, but other sources may be used as appropriate for the species. Codon optimization can also be performed to optimize expression, and expression vectors or mRNA can also be optimized for use.

The disclosure includes one or more of the following embodiments, in any combination(s) thereof:

A method of inducing stem cells to differentiate into beta cells or beta-like cells, said method comprising inducing the sequential expression of PDX1>NGN3>MAFA in a population of stem cells in order to reprogram said stem cells, and growing said reprogrammed cells until reprogrammed beta cells or beta-like cells form. This can be followed by induction of expression of NKX6.1 as well.

Any method herein described, wherein said stem cells are autologous stem cells, preferably autologous adipose derived stem cells, preferably from adult tissue.

Any method herein described, wherein said inducing step uses one or more expression vectors encoding PDX1, NGN3, and MAFA, preferably using a single inducible lentiviral or other vector encoding each of PDX1, NGN3, and MAFA under the control of different switches or inducible promoters that allow a sequential on/off activation of the respective expression vectors.

Any method herein described, wherein said inducing step requires 1 to 6 days of expression of a gene before activating the next gene in the sequence, or more preferably about 3 days.

Any method herein described, wherein said inducing step uses mRNA or circular mRNA encoding PDX1, NGN3, and MAFA.

An reprogrammed beta cell or beta-like cell made by a method described herein and producing insulin in response to glucose.

A composition comprising a population of reprogrammed beta cells or beta-like cells formed from stem cells transformed with expression constructs allowing the sequential expression of PDX1, NGN3, and MAFA, thus forming said reprogrammed cells able to produce insulin, but not glucagon, in response to high levels of glucose. Preferably, the cell population is enriched for the reprogrammed beta cells before use in patients.

A method of treating diabetes, by treating a patient with any of the reprogrammed beta cells described herein.

A method of treating diabetes, said method comprising obtaining stem cells from a patient with diabetes, inducing sequential expression of PDX1, NGN3, and MAFA, in said stem cells to form reprogrammed beta-cells, and introducing said reprogrammed beta cells into said patient.

A method of treating diabetes, said method comprising obtaining stem cells from a patient with diabetes, inducing sequential expression of PDX1>NGN3>MAFA, in said stem cells to form reprogrammed beta-cells, and introducing said reprogrammed beta cells into a pancreas of said patient.

A method of treating diabetes, said method comprising obtaining stem cells from a patient with diabetes, inducing sequential expression of PDX1>NGN3>MAFA, in said stem cells to form reprogrammed beta-cells, and introducing said reprogrammed beta cells into an artificial pancreas, and surgically placing said artificial pancreas into said patient.

As used herein, "inducing" the expression of certain genes in stem cells does not imply any particular methodology, and is not limited to the use of inducible promoters. Instead, any means of turning on gene expression can be used, including the use of expression vectors, naked DNA or RNA or protein, induced epigenetic changes, and the like. It does not include those natural cells that already demonstrate expression of the recited gene/proteins, but only stem cells that have been re-programmed to do so by the hand-of-man.

By "sequential" expression we mean that the initiation of transcription/translation is staggered, such that one begins before another. However, there may be overlap of transcription/translation times after initiation, e.g., co-expression.

In our experimental method, the expression order of genes (including PDX-1, NGN-3 and MAFA) was found to be important. Therefore, in our experimental design, we applied three different inducible promoters, one for each gene, for sequential expression of the three genes. In our experimental design, modeled from the development of pancreatic B-cells at the early stages of embryogenesis, there was little or no overlap in expression between the three genes. However, there remains the possibility of differentiation of stem cells to pancreatic beta-cells (with lower efficiency of differentiation and maturation) with some degree of co-expression of PDX-1, NGN-3 and MAFA.

As used herein, "stem cells" include a totipotent, pluripotent and multipotent stem cells. These are cells that are not yet differentiated, and thus can either form cells of all three germ layers and cell types, or a multiplicity of cell types upon receiving the appropriate signaling from its microenvironment. These cells can be isolated by appropriate means from the blood vessels of all tissues and organs.

As stem cells are small, early in their development stage, and are initially silenced cells, the majority of the scientific community characterizes stem cells incorrectly. These early cells do not express the surface markers typically believed to characterize stem cells such as CD34, CD44, CD90, or CD105 as reported in the literature. Instead, these stem cells express CD29, CD49, Nestin, Oct 4, Sca-1 and SSEA3/4 and markers of ABC cassette pumps such as ABCB5 and other early embryonic markers, without reprogramming of these cells to embryonic cells or making them related to the "cancer risk" iPS cells.

"Adult stem cells" are typically multipotent stem cells derived from a non-infant person, and does not imply any particular age. Also known as somatic stem cells, they can be found in children, as well as adults.

As used herein, "reprogrammed beta cells" or "beta-like cells" or "reprogrammed beta-like cells" are used interchangeably. These are cells that used to be to be naturally (not induced) toti-, multi-, or pluri-potent, but have been intentionally differentiated or "reprogrammed" by the methods described herein, and thus demonstrate the defining characteristic of being able to correctly secrete insulin, but not glucagon, in response to high glucose. The term does not include prior art partially differentiated cells that demonstrate incorrect regulation of insulin secretion, such as those described by Xu (2013) and Akinci (2013), or that co-secrete glucagon in response to glucose.

The reprogrammed beta cells may differ in other respects from wild type beta cells however, reflecting both the transfected genes as well as possible imperfections in the differentiation process.

As used herein, "autologous" means cells derived from the patient. "Allogenic" refers to cells derived from the same species, but having a different genotype. "Syngeneic" refers to cells from a genetically identical source, such as a twin, hence immunologically compatible or so closely related that transplantation does not provoke an immune response.

The "artificial pancreas" is a technology in development to help people with diabetes automatically control their blood glucose level by providing the substitute endocrine functionality of a healthy pancreas. Different approaches under consideration include:

1) The medical equipment approach—using an insulin pump under closed loop control using real-time data from a continuous blood glucose sensor.
2) The bioengineering approach—the development of a bio-artificial pancreas consisting of a biocompatible sheet of encapsulated beta cells. When surgically implanted, the islet sheet will behave as the endocrine pancreas and will be viable for years.
3) The gene therapy approach—the therapeutic infection of a diabetic person by a genetically engineered virus, which causes a DNA change of intestinal cells to become insulin-producing cells.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
|---|---|
| αMEM | MEM with Earles balanced salts |
| ADST | Adipose Tissue derived stem cells |
| cDNA | Copy DNA |
| DNA | Deoxyribonucleic acid |
| FBS | Fetal bovine serum |
| MEM | Minimum-essential medium |
| PBS | Phosphate buffered saline |
| PCR | Polymerase chain reaction |
| qPCR | Quantitative PCR |
| RNA | Ribonucleic acid |
| mRNA | Messenger RNA |

The following genes/proteins are discussed herein:
FAS: Fas Cell Surface Death Receptor, Previous symbol name: TNF Receptor Superfamily, Member 6 FAS (NM 000043)
FGF-10: Fibroblast Growth Factor-2
FGF-2: Fibroblast Growth Factor-2
FLIP: FLICE-like inhibitory protein, aka c-FLIP, now called CFLAR or CASP8 and FADD-like apoptosis regulator.
Fox- A1 and A2: Forhead Box a1 and a2
IL1B: interleukin 1 beta
ISL-1: ISELT-1 or ISL LIM homeobox 1
MAFA: v-maf avian musculoponeurotic fibrosarcoma oncogene homology A
Neuro D: Neuronal differentiation 1
NGN3: Neurogenin-1
NKX6.1: Nkx 6 homeobox1
PAX4, 6: Paired Box4
PDX1: Pancreatic and duodenal homeobox-1
Ptf1a: Pancreatic Specific transcription factor- 1A
SHH: Sonic hedgehog
CD29, Integrin beta-1 also known as CD29 is a protein that in humans is encoded by the ITGB1 gene
CD49, CD49a is an integrin alpha subunit.
Nestin, a type VI intermediate filament (IF) protein.
Sca-1 "Stem cells antigen-1". A common biological marker used to identify hematopoitic stem cell (HSC) along with other markers.
Oct-4, (octamer-binding transcription factor 4) also known as Aggeliki (POU domain, class 5, transcription factor 1) is a protein that in humans is encoded by the POU5F1 gene
SSEA3/4 Cell Surface Glycosphingolipids SSEA-3 and SSEA-4
ABCB5 belongs to the ATP-binding cassette (ABC) transporter superfamily of integral membrane proteins. ATP-binding cassette sub-family B member 5 also known as P-glycoprotein ABCB5 is a plasma membrane-spanning protein that in humans is encoded by the ABCB5 gene.

DETAILED DESCRIPTION

Figure 1:
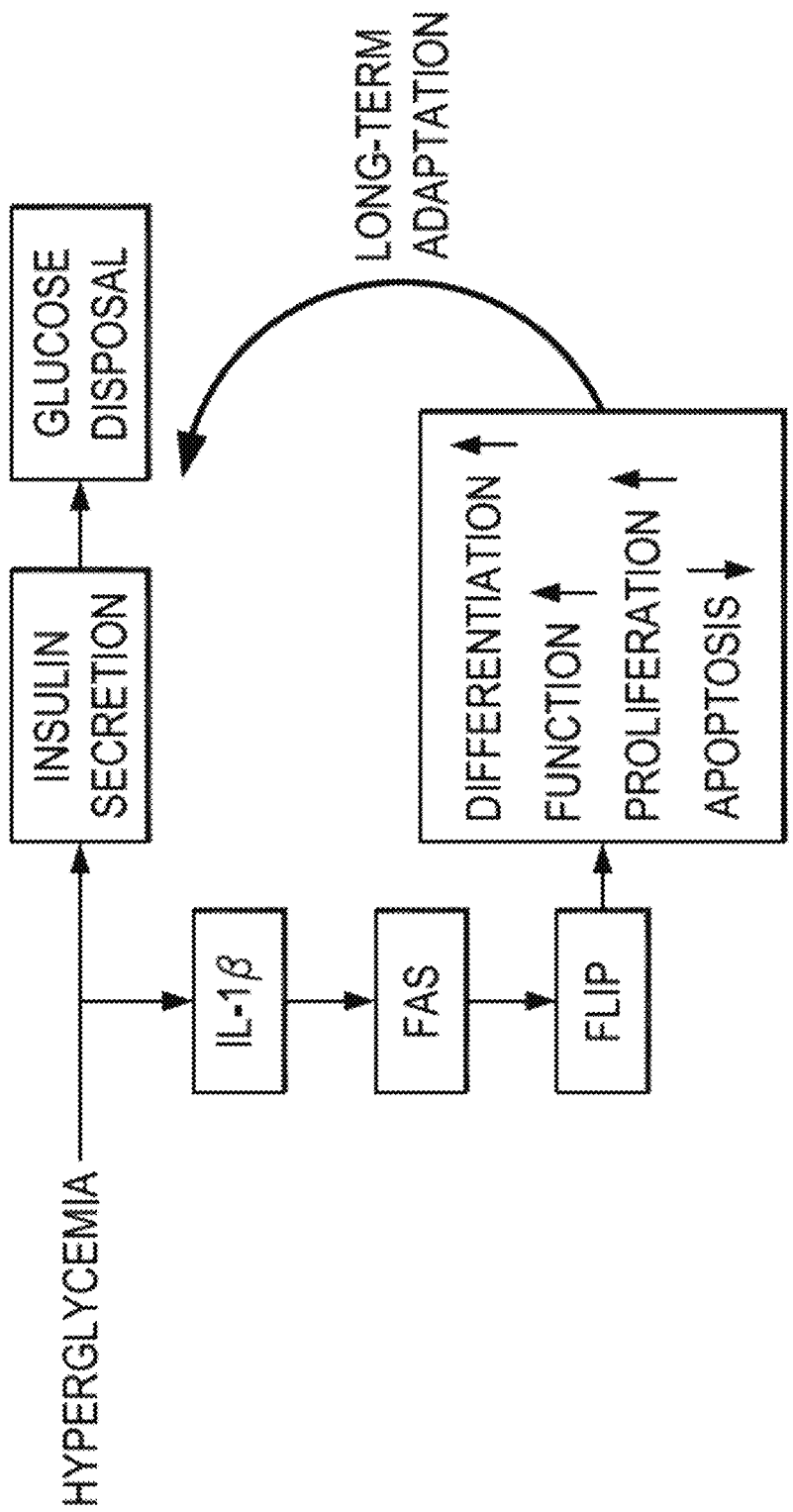
FIG. 1 Hypothetical model illustrating the consequence of hyperglycemia on β-cell production of IL-1β in parallel with insulin secretion. The paracrine effect of
IL-1β induces FAS engagement, which in the presence of c-FLIP leads to β-cell proliferation, differentiation, and increased function. From Donath 2005.
Figure 2:
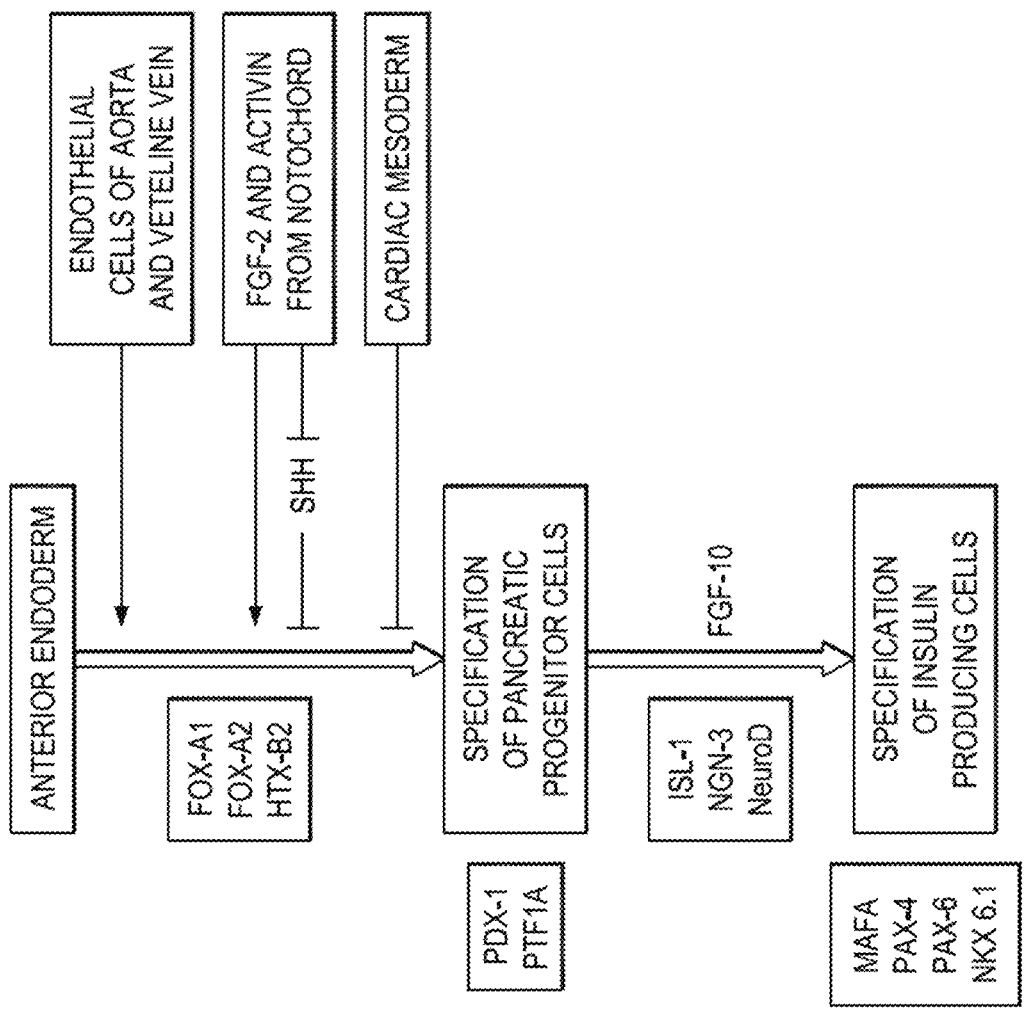
FIG. 2 Schematic representative of sequence of events and transcription factors involved in development of pancreatic beta-cells. According to our findings, the molecular transcription factors defined in green color, are the critical ones for the sequential induction of differentiation towards the insulin producing cells and differentiate from the other factors, such as ISL-1, that are existing in other developmental pathways and are not specific and critical for the pancreatic lineage commitment. LEGEND: Shh: Sonic hedgehog; Fox- a1 and a2: Forhead Box a1 and a2; FGF-2: Fibroblast Growth Factor-2; FGF-10: Fibroblast Growth Factor-2; Pdx-1:Pancreatic and duodenal homebox-1; Ptf1a: Pancreatic Specific transcription factor- 1A; ISL-1: ISELT-1 or ISL LIM homeobox 1; Ngn-3: Neurogenin-1; Neuro D: Neuronal differentiation 1: Mafa: v maf avian musculoponeurotic fibrosarcoma oncogenehomology A: Pax4, 6:Paired Box4; Nkx 6.1: Nkx 6 homebox1

To differentiate ADSCs into pancreatic islet cells, adipose tissue derived stem cells are transduced, transcribed, or translated sequentially, with different combinations of β-cell inducing factors, including PDX1, NGN3 and MAFA, such that the proteins appear in the differentiating cell sequentially (PDX1>NGN3>MAFA).

Although we used sequential transduction to demonstrate proof of concept, it may be preferred to use sequential activation of transcription, which would of course require three different inducible promoters. However, this will subject the cells to less trauma during the transduction or transfections, and may be preferred, depending on the method of nucleic acid transfer. In yet another embodiment, the promoters are chosen such that sufficient activation of the first differentiation factor will then induce the second, and so on. However, this is not yet accomplished herein. In yet another embodiment, the proteins themselves could be introduced sequentially, or mRNA encoding same.

Akinci (2013) attempted a similar experiment and did induce some differentiation towards beta cells. However, he did not use adult human stem cells but rather a rat pancreatic exocrine cell line (AR42J-B13). In addition, this group transfected all three genes at the same time and not sequentially, as described herein. They were thus unable to achieve glucose sensitive secretion of insulin, although they could at least induce insulin production.

Oh (2015) used exosomes from insulinoma derived cell lines to induce differentiation of bone marrow cells. However, insulinoma is a semi-malignant form of a pancreas tumor, and therefor present risk that not only the features of the beta cells are brought forward by the exosomes, but that they also could generate new insulinomas. Our own experiments confirm that the addition of exosomes from breast cancer cells to normal adipose derived stem cells significantly changes their gene expression profile and their features in direction of invasiveness and tumor formation. Thus, the use of exosomes from insulinoma derived cell lines is clinically unacceptable for safety reasons.

Millman (2015) used patient-derived human induced pluripotent stem cells from skin fibroblasts using sequential use of various factors (different from those discussed herein) in the media. The resulting cells were able to secrete insulin in response to glucose, and few cells expressed the α-cell hormone glucagon. However, as noted herein, induced pluripotent cells are believed to have evolved in the direction of tumorigenesis, and thus present significant safety risks.

Lima (2016) studied the use of a variety of transcription factors, including Pdx1, Ngn3, MafA and Pax4, added at the same time to exocrine tissue cells isolated from the pancreas of brain dead donors. Lima found that most efficient TF combination for the ex vivo reprogramming of exocrine pancreatic cells towards β-cells resulted from the concerted actions of Pdx1, Ngn3, MafA and Pax4. Inclusion of Pax4 appeared to be crucial for generating glucose responsive beta-like cells. Those cells, however, expressed insulin at about 15-30% of the levels in human islets. Inclusion of late stage inhibition of ARX using siRNA significantly decreased glucagon mRNA and protein levels, making these reprogrammed cells promising. However, such cells were not autologous, and thus rejection remains problematic.

Xu (2013) was able to demonstrate that the co-expression of PDX1 and MAFA during a specific time window of development can act synergistically with either NGN3 or NEUROD to promote the differentiation of mouse embryonic stem cells into insulin-secreting cells. This group showed co-expression of PDX1 and MAFA with either NGN3 or NEUROD at the final stage of a three-step differentiation process, significantly increased the differentiation efficiency. It also increased the glucose-stimulated insulin and C-peptide secretion in insulin-secreting cells derived from mouse embryonic stem cells (mES cells) compared to the control green fluorescent protein (GFP) vector-transduced group. Unfortunately, neither embryonic stem cells nor induced pluripotent cells (iPS) can be used for clinical applications due to the existing risk of tumorigenesis.

Further, although staging the differentiation process, the Xu group still used co-expression of the above factors, not sequential expression. Thus, mES cells were first induced to make embryoid bodies for 48 hours, then stimulated using activin A for 2 days. Second, those cells were expanded using fibroblast growth factor and epidermal growth factor for 5 days. Third, the cells were then matured and the differentiation factors adding alone, in pairs, in triplet combinations and all four at once for another 5 days. The two factor groups increased insulin 1 levels by 3-fold, but the three factor groups increased expression 15-fold. No further increase was observed with the fourth factor.

In contrast, using sequential expression of PDX1 (3 or more days) before initiating NGN3 expression (3 or more days) and then finally initiating MAFA expression (continuous expression thereafter), we were able to produce highly functional insulin producing cells from initially unmodified adult stem cells (not embryonic or induced pluripotent stem cells).

Although our experiments used 3 or more days before initiating the next differentiation factor, this length of time can vary (e.g., 1-10 days), possibly being reduced in healthier cells or where the differentiation factors have very strong promoters and well optimized expression vectors or other vehicles. By contrast, where the cells are weaker or are recovering from the shock of a transfection or transduction procedure, or where the expression vectors are not optimized, then longer periods may be needed. Thus, the time period can vary from 12 hour to 10 days or more, preferably at least 24, 36, 48, 72, 96 or 120 hours or more. We also contemplate that our results can be improved by optimizing the expression time for each gene for optimal differentiation results.

Figure 4:
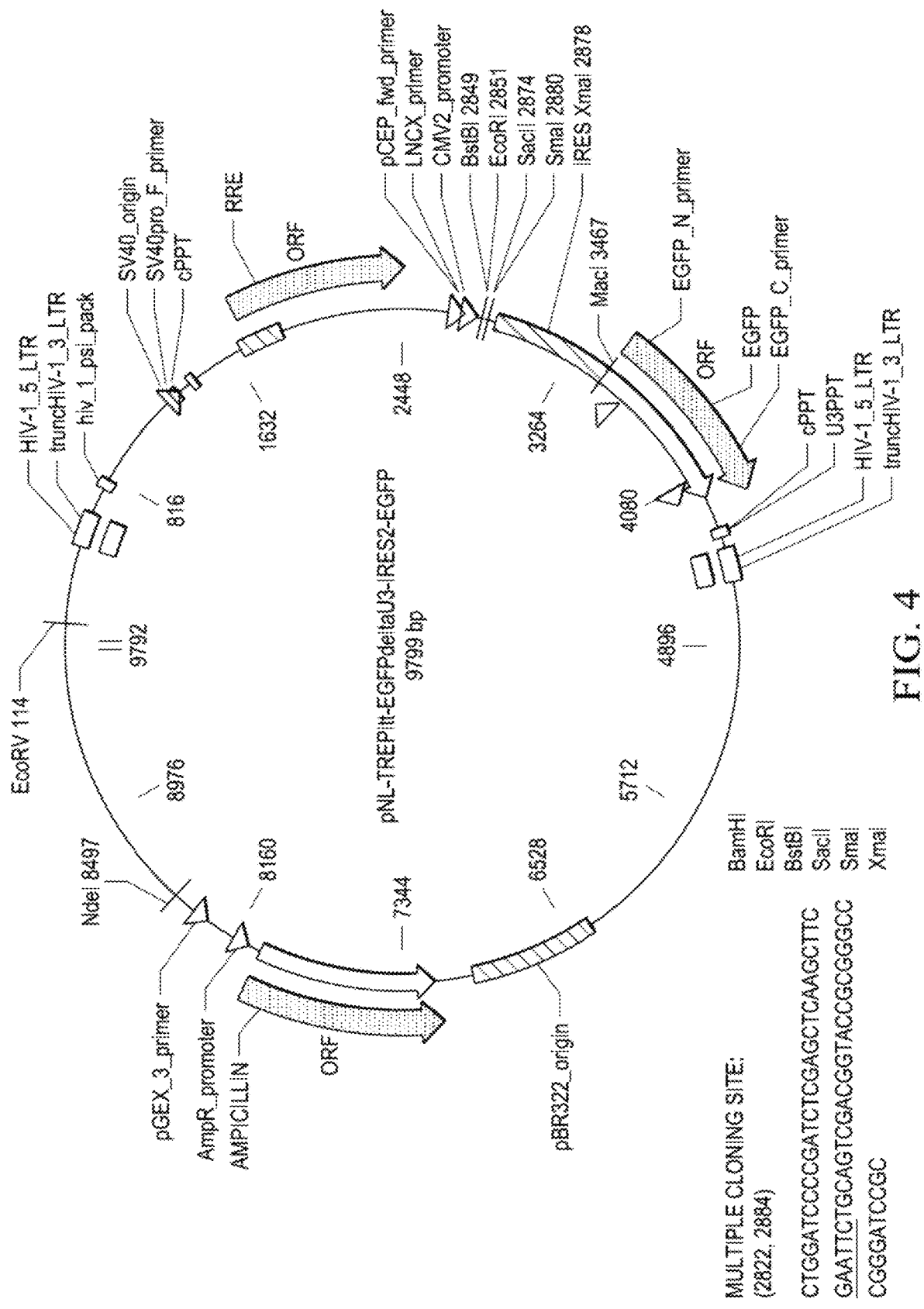
FIG. 4 Exemplary vector. PNL-TREPiTT-EGFP deltaU3-IRES2-EGFP (AddGene No 18659) plasmid was used as the backbone vector for each of the PDX1, NGN3 and MAFA constructs. Other vectors have also been used, but are not described herein.

We used lentivirus as a transduction system, but this is exemplary only and other methods or vectors could be used. The lentiviral vector includes packing vector psPAX2 (AddGene, 12260) and envelope vector pMD2.G (AddGene, 12259) (Isaias, 2012). In addition a doxycycline controlled transactivator (rtTA 3) (pLenti CMV rtTA3, Addgene, 26429) was used as a transcriptional inductive switch of the system. Plasmid PNL-TREPiTT-EGFP delta U3-IRES2-EGFP (FIG. 4) was the backbone vector for the genes.

Figure 3:
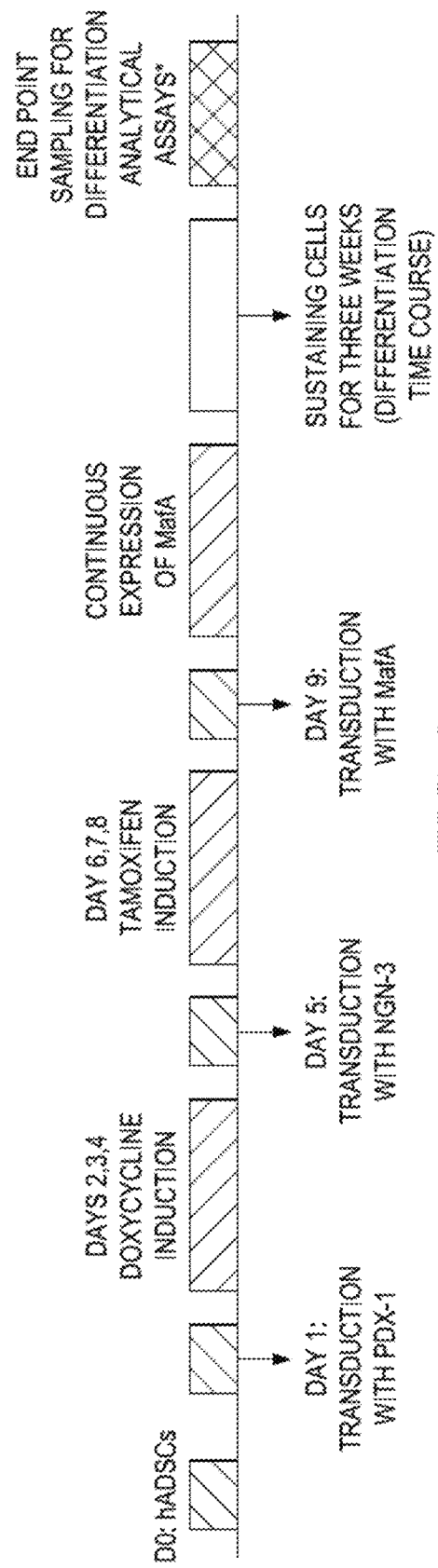
FIG. 3 Time course of transductions and sequential expression used in our experiments.

In our first effort, we used one switch (doxycycline) for all three genes, which were sequentially introduced into cells. Later, however, we used 2 more plasmids including a plasmid containing NGN-3 gene under the control of tamoxifen switch, and MAFA plasmid with a constitutive promoter. Thus, we could use different inducers to turn the genes on at different time points. We applied a doxycycline switch for upregulation of PDX-1, a tamoxifen switch for upregulation of NGN-3, and MafA had continuous expression by using a normal constitutive expression vector. For the expression time points, see FIG. 3.

Figure 5:
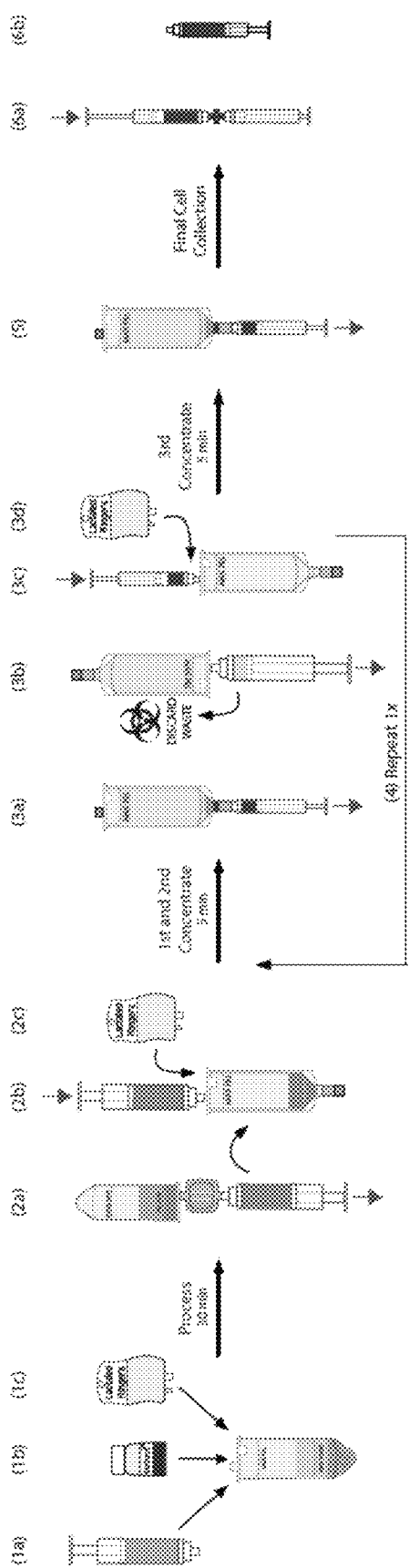
FIG. 5 Schematic of method of preparing ADSCs.

Human subcutaneous adipose tissue was obtained from patients undergoing elective lipoaspiration with informed consent and ADSCs produced as shown in FIG. 5. 1a. Load adipose tissue in each Processing Tube up to MAX TISSUE line. 1b. Add 2.5 mL reconstituted Matrase™ per tube using 10 mL syringe. 1c. Add preheated Ringer's to each tube upto MAX FILL line using 60 mL Lactated Ringers Syringe. 2a. Filter processed tissue into 60 mL Tissue Syringe. 2b. Transfer filtered tissue into Wash Tube. 2c. Add Ringer's to MAX FILL line using 60 mL Lactated Ringers Syringe. 3a. Extract 1.5 mL Cells with 3 mL syringe. 3b. Extract remaining liquid with 60 mL Tissue Syringe. Discard in sterile waste container. 3c. Return cells to Wash Tube. 3d. Add Ringer's to MAX FILL line using 60 mL Lactated Ringers Syringe. 4. Repeat Concentrate and 3a-3d one time using same syringes from steps 3a-3d. 5. Extract 3 mL cells with 3 mL syringe from step 3a. 6a. Push cells through luer coupler into new 3 mL syringe to disrupt clumps. 6b. Cells are now available for use at the physician's discretion. In brief, adipose tissue was washed thoroughly, minced, and incubated with Ringers lactate containing a combination of collagenase I and II and a neutral protease (Matrase™ Reagent, InGeneron Inc., Houston TX) in a Tissue Processing Unit (Transpose RT™ System, InGeneron Inc.) for 30 minutes at 40° C. Subsequently, the cell suspension was filtered through a 100-µm filter, washed twice, and then centrifuged at 600 rpm for 5 minutes. The adipose stromal vascular fraction was resuspended in αMEM with 20% FBS, L-glutamine, and penicillin-streptomycin-amphotericin B (SigmaAldrich®) at 37° C. in 5% CO2. Red blood cells in the supernatant and nonadherent cells were removed after 48 hours. For all experiments shown, human subcutaneous adipose tissue-derived cells were used prior to passage 6.

If desired, ADSCs can be further enriched using ADSC specific markers. The separation of adipocyte precursor populations from nonadipogenic cells using a single cell surface marker is almost impossible, but with the help of multicolor flow cytometry, these putative progenitor cells can be differentiated from nonadipogenic cells such as endothelial and blood cells. The markers include CD29, CD49, Nestin, Oct 4, Sca-1 and SSEA3/4 and markers of ABC cassette pumps such as ABCB5. Beta-like cells can also be enriched after reprogramming in a similar manner, but using beta cell specific markers, and/or can be further amplified in culture.

The commercially available cell line 293FT cells was used for viral packaging. The 293FT cell line is a fast-growing, highly transfectable clonal isolate derived from human embryonal kidney cells transformed with the SV40 large T antigen. When an expression vector and a packaging mix are co-transfected into 293FT cells, high levels of the viral RNA and the gag/pol and rev proteins required for packaging are produced.

Briefly viral particles produced in 293FT cells were packaged with psPAX2, pMD2.G vectors and plasmids encoding PDX1, NGN3 and MAFA. Reprogramming of about 80% confluent ADSCs into proliferative state was accomplished by sequential transduction with the viral particles containing PDX1, NGN3 and MAFA vectors.

Transfected cells were cultivated in large tissue culture plates in α-MEM media (Invitrogen) supplemented with 5% (vol/vol) horse serum, 0.1 mM non-essential amino acids, and 2 mM L-glutamate (Islas, 2012).

Total RNA was isolated, and cDNA prepared and amplified as described previously. Quantitative real-time RT-PCR was performed using ABI Prism 7000 sequence Detection system (Applied Biosystems, Foster City, Calif., USA) according to the manufacturers' protocol. The primer sets for the human ADSCs' used initially in this study include:

```
PDX1:
                                    (SEQ ID NO. 1)
F: CCAGTT TGCAGGC TCGCTGG
                                    (SEQ ID NO. 2)
R: GCTGCGTATGCA CCTCCTGC

NKX6.1:
                                    (SEQ ID NO. 3)
F: AGAGCACGCTTG GCC TAT TC
                                    (SEQ ID NO. 4)
R: GGA ACCAGACCT TGACCTGACT

GK:
                                    (SEQ ID NO. 5)
F: CAT CTCTGAGTGCATCTCCGACT
                                    (SEQ ID NO. 6)
R: TCGCAGTGATGGTCTT CGT AGTA

GLUT-2:
                                    (SEQ ID NO. 7)
F: TCCAGCTACCGACAGCCTATT
                                    (SEQ ID NO. 8)
R: CCAGCCGTCTGAAAAATGCT

INS:
                                    (SEQ ID NO. 9)
F: GCAGCCTTTGT GAACCAACA
                                    (SEQ ID NO. 10)
R: CGGGTCTTGGGTGTGT AGAAGAAG

MAF-A:
                                    (SEQ ID NO. 11)
F: AGCAGCGGCACATTCTGG
                                    (SEQ ID NO. 12)
R: TTGTACAGG TCC CGCTCTTTG

MAF-B:
                                    (SEQ ID NO. 13)
F: CGCCTCCTAGACTCGAGC AG
                                    (SEQ ID NO. 14)
R: GAGTCTCCAGATGGCCTTGGT

MYT-1:
                                    (SEQ ID NO. 15)
F: TGAAG AATG AAGGACCGACC
                                    (SEQ ID NO. 16)
R: TTTCCAGCAAAGGTTGCT CT

NEUROD-1:
                                    (SEQ ID NO. 17)
F: ATGACCAAATCGTACAGCGAG
                                    (SEQ ID NO. 18)
R: GT TCATGGCTTCGAGGTCGT

NGN3:
                                    (SEQ ID NO. 19)
F: ACCCCATTCTC TCTTCTTTTCTC CT
                                    (SEQ ID NO. 20)
R: GAG GCGTCATCCTTTCTACCG

PAX-4:
                                    (SEQ ID NO. 21)
F: CAGAGGCACTGGAGAA AGAGTTC
                                    (SEQ ID NO. 22)
R: GGGCT TGAGAC AGGCTTTAGG

PAX-6:
                                    (SEQ ID NO. 23)
F: CGAATTCTGCA GGT GTCCAA
                                    (SEQ ID NO. 24)
R: ACAGACCCCCTCGGACAGTAAT

PC1/3:
                                    (SEQ ID NO. 25)
F: CTCTGGCTG CTGGCATCT
                                    (SEQ ID NO. 26)
R: CTGCATATCTCGCCAG GTG

PC2:
                                    (SEQ ID NO. 27)
F: GAGAAGACGCAGCCTACACC
                                    (SEQ ID NO. 28)
R: CTGCAA AGCCATCTTTACCC

PDX1:
                                    (SEQ ID NO. 29)
F: CCATGGATGAAGTCTA CCA
                                    (SEQ ID NO. 30)
R: GTGCGCGTCCGCTTGTTCTC

SCG2:
                                    (SEQ ID NO. 31)
F: GGAG GAATATGCTGTGGAGCTC
                                    (SEQ ID NO. 32)
R: CAGCCCCAGAGATGA GGAAA

SGNE-1:
                                    (SEQ ID NO. 33)
F: GACCGGGTCTCAGAAGCAGATA
                                    (SEQ ID NO. 34)
R: AGTCAACTCTGCCACGATGTT

SST:
                                    (SEQ ID NO. 35)
F: ATGATGCCCTG GAACCTGAAG
                                    (SEQ ID NO. 36)
R: GCCGGGTTTGAGTTAGCAGAT
```

Our future work will likely use a single vector encoding 3 genes under different inducible promoters. In addition, a promoter reporter system can be used in the future to select and enrich the differentiated beta cells, although these experiments are not yet complete. To this end, cells can be infected with a plasmids containing e.g., NKX6.1 neomycin resistant gene and insulin 1-m-cherry promoter reporters. Therefore, differentiated B-cells, which are expressing NKX-6.1 can be selected and enriched by addition of neomycin to the media. In the next step, insulin producing cells also can be enriched by FACS sorting those cells expressing the red color of the m-cherry.

Future work will also include confirmatory experiments to demonstrate accurate response to glucose using patch clamp experiments. Patch-clamp recordings of adenovirus-infected cells are performed according to a routine protocol. The extracellular solution contains Na-acetate (140 mM), CaCl$_2$ (1 mM), MgCl$_2$ (1 mM), HEPES (10 mM) (pH 7.4, adjusted with NaOH) and TTX 0.5 mM (blocks the sodium channel), and nisoldipine 200 nM (eliminates the L-type calcium current). Glucose 20 mM will be added to the superfusing solution.

The current will be recorded with Axopatch 2B amplifier (Axon Instruments, Union City, Calif.), and data acquisition and pulse sequence analysis performed with pCLAMP software suite (Version 8.0, Axon). Data acquisition is initiated when the whole-cell patch is formed and stable; the holding potential set at 80 mV, and different depolarizing potentials (with 10 mV step and 6 sec interval, each lasting for 80 ms) attempted (each lasting for 20 ms) to evoke ion channel opening (Li et al., 2007). hMSCs were used as the standard control.

Future work will also include rescuing diabetic mice models with the newly reprogrammed beta-like cells. Six- to eight-week-old BALB/c transgenic mice that modified for conditional expression of luciferase under the control of the Insulin-1 gene, are made hyperglycemic by i.p. injection of streptozotocin (STZ; Sigma) at 220 mg/kg of body weight. When blood glucose reach levels >16.7 mmol/L and are maintained stably for 1 week, mice are transplanted with $2 \times 10^6$ of the reprogrammed pancreatic beta-cells in 0.1 ml PBS under the renal capsule.

Blood glucose levels will be monitored twice a week in samples obtained from the tail vein of mice by using Accutrend strips (Roche Diagnostics, Indianapolis, Ind.). Grafts are removed after 14 days, and analyzed by immune-histochemistry for the presence of insulin producing cells. Mice are monitored 1 day later for changes in blood glucose levels. Serum is collected from the orbital plexus of mice for human C-peptide levels analysis. The ultrasensitive human C-peptide ELISA kit (Mercodia) with 3% cross reactivity to proinsulin but no cross reactivity to mouse C-peptide and mouse insulin ELISA kit is used according to the manufacturer's instruction.

For intraperitoneal glucose tolerance test (IPGTT), normal non-diabetic mice (n=4) and diabetic mice (n=4) with normalized glucose levels following the transgenic cell transplantation are fasted for 6 h and then given an i.p. injection of glucose (2 g/kg of body weight). Blood glucose is monitored at 0, 30, 60, 90, and 120 min after the glucose injection (Li, 2007, Gefen, 2010).

Once the mice experiments confirm safety and efficacy, trials can be initiated in humans, but this is expected to require 2-5 years of additional work.

Each of the following references are incorporated by reference herein in its entirety for all purposes:

Akinci, E., et al. "Reprogramming of pancreatic exocrine cells towards a beta (β) cell character using Pdx1, Ngn3 and MafA," *Biochemical Journal*, 442(3): 539-550 (2013).

Ameri, J. et al., "FGF-2 Specifies hESC-Derived Definitive Endoderm Into Forgut/Midgut Cell Lineages In A Concentration Dependent Manner," *Stem Cells* 28, 45-56 (2010).

Arda, H.E., et al., "Gene Regulatory Networks Governing Pancreas Development," *Developmental Cell* 25, 5-13 (2013).

Bai et al., "Tracking Long Term Survival Of Intramyocardially Delivered Human Adipose Tissue Derived Stem Cells Using Bioluminescence Imaging," *Mol Imaging Biol.* 13 (4), 633-45 (2011).

Benitez, C.M., et al., "Deconstructing pancreas developmental biology," *Perspect Biol.* 4, 1-17 (2012).

Cheng, X., et al., "Self Renewing Endodermal Progenitor Lines Generated From Human Pluripotent Stem Cells," *Cell Stem Cell* 10, 371- 384 (2012).

Donath M.Y., et al., "Mechanisms of β-Cell Death in Type 2 Diabetes," *Diabetes* 54(s2): S108-S113 (2005).

Francis M.P., et al., "Isolating adipose-derived mesenchymal stem cells from lipoaspirate blood and saline fraction," *Organogenesis* 6(1): 11-14 (2010).

Gefen-Halevi, S., et al., "Nkx 6.1 Promotes PDX1 Induced Liver To Pancreatic B-Cells Programming," *Cellular Reprogramming* 12 (6), 655- 664 (2010).

Gilbert, S.F., Developmental Biology, 9th edition, 2010, Sinauer Association, Inc. Sunderland, Mass., USA.

Gittes, G.K., "Developmental Biology of the Pancreas: A comprehensive review," *Developmental Biology* 326, 4-35 (2009).

Greggio, C., "Artificial three- dimensional niches deconstruct pancreas development in vitro," *Development* 140 (121), 4452- 4462 (2013).

Hebrok, M., "Hedgehog signaling in pancreas development", *Mech. Dev.* 120 (1), 45-57 (2003).

Islas, J.F. et al., "Transcription factors ETS2 and MESP1 transdifferentiate human dermal fibroblasts into cardiac progenitors," *Proc. Natl. Acad. Sci.* 109 (32), 13016- 21 (2012).

Kroon, E., et al., "Pancreatic endoderm derived from human embryonic stem cells generates glucose- responsive insulin secreting cells in vivo." *Nat. Biotechnol.* 26, 443- 452 (2008).

Li, Y., et al., "Generation of Insulin- Producing cells from PDX1 Gene-Modified Human Mesenchymal Stem Cells," *J. Cell. Physiol.* 211, 36- 44 (2007).

Lima M.J., et al., "Generation of Functional Beta-Like Cells from Human Exocrine Pancreas," *PLoS ONE* 11(5): e0156204 (2016).

Millman, J.R., et al., "Generation of stem cell-derived b-cells from patients with type 1 diabetes," *NATURE COMMUNICATIONS* 7:11463 (2016).

Offield M.F., et al., "PDX1 is required for pancreatic outgrowth and differentiation of the rostral duodenum," *Development* 122, 983-995 (1996).

Oh K., et al., "In Vivo Differentiation of Therapeutic Insulin-Producing Cells from Bone Marrow Cells via Extracellular Vesicle-Mimetic Nanovesicles," *ACS Nano* 9(12): 11718-27 (2015).

Schaffer, A.E., et al., "Nkx 6.1 controls a gene regulatory network required for establishing and maintaining pancreatic Beta cell identity," *PLOS Genetics* 9 (1), 1- 15 (2013).

Wankhade, U.D., et al., "Advances in Adipose-Derived Stem Cells Isolation, Characterization, and Application in Regenerative Tissue Engineering," *Stem Cells Int.*, 2016: 3206807 (2016).

Xu, H., et al., "The combined expression of Pdx1 and MafA with either Ngn3 or NeuroD improves the differentiation efficiency of mouse embryonic stem cells into insulin-producing cells," *Cell Transplant.* 22(1):147-58 (2013).

The invention claimed is:

1. A method of inducing stem cells to differentiate into beta cells, said method comprising (a) obtaining a population of unmodified adult somatic stem cells, (b) introducing at least one vector encoding inducible expression of pancreatic and duodenal homeobox 1 ("PDX1"), Neurogenin 3 ("NGN3"), and v-maf avian musculoponeurotic fibrosarcoma oncogene homology A ("MAFA") into said unmodified adult somatic stem cells; (c) inducing a sequential expression of genes encoding PDX1 1-10 days before inducing NGN3, and inducing NGN3 1-10 days before inducing MAFA in said stem cells by said at least one vector to form reprogrammed stem cells, and (d) growing said reprogrammed stem cells until differentiated beta cells form, wherein said genes are continuously expressed after being induced.

2. A method of inducing stem cells to differentiate into beta cells, said method comprising (a) obtaining adult stem cells from a patient, (b) introducing at least one vector encoding inducible expression of PDX1, NGN3 and MAFA into said adult stem cells, (c) inducing the sequential expression of genes encoding PDX1 at least 1 day before inducing NGN3, and inducing NGN3 expression at least 1 day before inducing MAFA in said adult stem cells using said at least one vector in order to reprogram said adult stem cells, and (d) growing said reprogrammed stem cells until differentiated beta cells form, and wherein said genes are continuously expressed after being induced.

3. The method of claim 1, comprising subsequent inducement of expression of a gene encoding NKX6.1 1-10 days after inducing MAFA.

4. The method of claim 1, wherein said stem cells are autologous stem cells.

5. The method of claim 1, wherein said stem cells are autologous adipose derived stem cells.

6. The method of claim 2, wherein said stem cells are adipose derived stem cells.

7. The method of claim 1, wherein said inducing step uses one or more expression vectors encoding PDX1, NGN3, and MAFA.

8. The method of claim 1, wherein said inducing step uses one or more viral vectors encoding PDX1, NGN3, and MAFA.

9. The method of claim 1, wherein said inducing step uses mRNA encoding PDX1, NGN3, and MAFA.

10. The method of claim 1, wherein PDX1, NGN3, and MAFA are each expressed for 1 to 6 days before initiating a next gene.

11. The method of claim 1, wherein PDX1, NGN3, and MAFA are each expressed for about 3 days before initiating a next gene.

12. A method of treating diabetes, comprising introducing said reprogrammed beta cells of claim 1 into a patient.

13. A method of treating diabetes, comprising introducing said reprogrammed beta cells of claim 1 into said patient.

14. The method of claim 13, comprising introducing said reprogrammed beta cells into a pancreas of said patient.

15. A method of claim 13, comprising introducing said reprogrammed beta cells into an artificial pancreas, and surgically placing said artificial pancreas into said patient.

16. A method of treating diabetes, said method comprising introducing said reprogrammed beta cells of claim 2 into said patient.

* * * * *

SEQUENCE LISTING

<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: DNA Primer

<400> SEQUENCE: 1
ccagtttgca ggctcgctgg                                                     20

<210> SEQ ID NO 2
<211> LENGTH: 20
<212> TYPE: DNA
<213> ORGANISM: Artificial Sequence
<220> FEATURE:
<223> OTHER INFORMATION: PCR Primer

<400> SEQUENCE: 2
gctgcgtatg cacctcctgc                                                     20

<210> SEQ ID NO 3
<211> LENGTH: 20
<212> TYPE: DNA
<213> ORGANISM: Artificial Sequence
<220> FEATURE:
<223> OTHER INFORMATION: PCR Primer

<400> SEQUENCE: 3
agagcacgct tggcctattc                                                     20

<210> SEQ ID NO 4
<211> LENGTH: 22
<212> TYPE: DNA
<213> ORGANISM: Artificial Sequence
<220> FEATURE:
<223> OTHER INFORMATION: PCR Primer

<400> SEQUENCE: 4
ggaaccagac cttgacctga ct                                                  22

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5
catctctgag tgcatctccg act                                                 23

<210> SEQ ID NO 6
<211> LENGTH: 23
<212> TYPE: DNA
<213> ORGANISM: Artificial Sequence
<220> FEATURE:
<223> OTHER INFORMATION: PCR primer

<400> SEQUENCE: 6
tcgcagtgat ggtcttcgta gta                                                 23

<210> SEQ ID NO 7
<211> LENGTH: 21
<212> TYPE: DNA
<213> ORGANISM: Artificial Sequence

```
<220> FEATURE:
<223> OTHER INFORMATION: PCR Primer

<400> SEQUENCE: 7
tccagctacc gacagcctat t                                             21

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
ccagccgtct gaaaaatgct                                               20

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gcagcctttg tgaaccaaca                                               20

<210> SEQ ID NO 10
<211> LENGTH: 24
<212> TYPE: DNA
<213> ORGANISM: Artificial Sequence
<220> FEATURE:
<223> OTHER INFORMATION: PCR Primer

<400> SEQUENCE: 10
cgggtcttgg gtgtgtagaa gaag                                          24

<210> SEQ ID NO 11
<211> LENGTH: 18
<212> TYPE: DNA
<213> ORGANISM: Artificial Sequence
<220> FEATURE:
<223> OTHER INFORMATION: PCR Primer

<400> SEQUENCE: 11
agcagcggca cattctgg                                                 18

<210> SEQ ID NO 12
<211> LENGTH: 21
<212> TYPE: DNA
<213> ORGANISM: Artificial Sequence
<220> FEATURE:
<223> OTHER INFORMATION: PCR Primer

<400> SEQUENCE: 12
ttgtacaggt cccgctcttt g                                             21

<210> SEQ ID NO 13
<211> LENGTH: 20
<212> TYPE: DNA
<213> ORGANISM: Artificial Sequence
<220> FEATURE:
<223> OTHER INFORMATION: PCR Primer

<400> SEQUENCE: 13
cgcctcctag actcgagcag                                               20
```

<210> SEQ ID NO 14
<211> LENGTH: 21
<212> TYPE: DNA
<213> ORGANISM: Artificial Sequence
<220> FEATURE:
<223> OTHER INFORMATION: PCR Primer

<400> SEQUENCE: 14
gagtctccag atggccttgg t                                         21

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
tgaagaatga aggaccgacc                                           20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
tttccagcaa aggttgctct                                           20

<210> SEQ ID NO 17
<211> LENGTH: 21
<212> TYPE: DNA
<213> ORGANISM: Artificial Sequence
<220> FEATURE:
<223> OTHER INFORMATION: PCR Primer

<400> SEQUENCE: 17
atgaccaaat cgtacagcga g                                         21

<210> SEQ ID NO 18
<211> LENGTH: 20
<212> TYPE: DNA
<213> ORGANISM: Artificial Sequence
<220> FEATURE:
<223> OTHER INFORMATION: PCR Primer

<400> SEQUENCE: 18
gttcatggct tcgaggtcgt                                           20

<210> SEQ ID NO 19
<211> LENGTH: 25
<212> TYPE: DNA
<213> ORGANISM: Artificial Sequence
<220> FEATURE:
<223> OTHER INFORMATION: PCR Primer

<400> SEQUENCE: 19
accccattct ctcttctttt ctcct                                     25

<210> SEQ ID NO 20
<211> LENGTH: 21
<212> TYPE: DNA
<213> ORGANISM: Artificial Sequence
<220> FEATURE:
<223> OTHER INFORMATION: PCR Primer

<400> SEQUENCE: 20
gaggcgtcat cctttctacc g                                        21

<210> SEQ ID NO 21
<211> LENGTH: 23
<212> TYPE: DNA
<213> ORGANISM: Artificial Sequence
<220> FEATURE:
<223> OTHER INFORMATION: PCR Primer

<400> SEQUENCE: 21
cagaggcact ggagaaagag ttc                                      23

<210> SEQ ID NO 22
<211> LENGTH: 21
<212> TYPE: DNA
<213> ORGANISM: Artificial Sequence
<220> FEATURE:
<223> OTHER INFORMATION: PCR Primer

<400> SEQUENCE: 22
gggcttgaga caggctttag g                                        21

<210> SEQ ID NO 23
<211> LENGTH: 20
<212> TYPE: DNA
<213> ORGANISM: Artificial Sequence
<220> FEATURE:
<223> OTHER INFORMATION: PCR Primer

<400> SEQUENCE: 23
cgaattctgc aggtgtccaa                                          20

<210> SEQ ID NO 24
<211> LENGTH: 22
<212> TYPE: DNA
<213> ORGANISM: Artificial Sequence
<220> FEATURE:
<223> OTHER INFORMATION: PCR Primer

<400> SEQUENCE: 24
acagaccccc tcggacagta at                                       22

<210> SEQ ID NO 25
<211> LENGTH: 18
<212> TYPE: DNA
<213> ORGANISM: Artificial Sequence
<220> FEATURE:
<223> OTHER INFORMATION: PCR Primer

<400> SEQUENCE: 25
ctctggctgc tggcatct                                            18

<210> SEQ ID NO 26
<211> LENGTH: 19
<212> TYPE: DNA
<213> ORGANISM: Artificial Sequence
<220> FEATURE:
<223> OTHER INFORMATION: PCR Primer

<400> SEQUENCE: 26
ctgcatatct cgccaggtg                                           19

<210> SEQ ID NO 27

```
<210> SEQ ID NO 27
<211> LENGTH: 20
<212> TYPE: DNA
<213> ORGANISM: Artificial Sequence
<220> FEATURE:
<223> OTHER INFORMATION: PCR Primer

<400> SEQUENCE: 27
gagaagacgc agcctacacc                                              20

<210> SEQ ID NO 28
<211> LENGTH: 20
<212> TYPE: DNA
<213> ORGANISM: Artificial Sequence
<220> FEATURE:
<223> OTHER INFORMATION: PCR Primer

<400> SEQUENCE: 28
ctgcaaagcc atctttaccc                                              20

<210> SEQ ID NO 29
<211> LENGTH: 19
<212> TYPE: DNA
<213> ORGANISM: Artificial Sequence
<220> FEATURE:
<223> OTHER INFORMATION: PCR Primer

<400> SEQUENCE: 29
ccatggatga agtctacca                                               19

<210> SEQ ID NO 30
<211> LENGTH: 20
<212> TYPE: DNA
<213> ORGANISM: Artificial Sequence
<220> FEATURE:
<223> OTHER INFORMATION: PCR Primer

<400> SEQUENCE: 30
gtgcgcgtcc gcttgttctc                                              20

<210> SEQ ID NO 31
<211> LENGTH: 22
<212> TYPE: DNA
<213> ORGANISM: Artificial Sequence
<220> FEATURE:
<223> OTHER INFORMATION: PCR Primer

<400> SEQUENCE: 31
ggaggaatat gctgtggagc tc                                           22

<210> SEQ ID NO 32
<211> LENGTH: 20
<212> TYPE: DNA
<213> ORGANISM: Artificial Sequence
<220> FEATURE:
<223> OTHER INFORMATION: PCR Primer

<400> SEQUENCE: 32
cagccccaga gatgaggaaa                                              20

<210> SEQ ID NO 33
<211> LENGTH: 22
<212> TYPE: DNA
<213> ORGANISM: Artificial Sequence
<220> FEATURE:
<223> OTHER INFORMATION: PCR Primer

<400> SEQUENCE: 33
```

```
gaccgggtct cagaagcaga ta                                          22

<210> SEQ ID NO 34
<211> LENGTH: 21
<212> TYPE: DNA
<213> ORGANISM: Artificial Sequence
<220> FEATURE:
<223> OTHER INFORMATION: PCR Primer

<400> SEQUENCE: 34
agtcaactct gccacgatgt t                                           21

<210> SEQ ID NO 35
<211> LENGTH: 21
<212> TYPE: DNA
<213> ORGANISM: Artificial Sequence
<220> FEATURE:
<223> OTHER INFORMATION: PCR Primer

<400> SEQUENCE: 35
atgatgccct ggaacctgaa g                                           21

<210> SEQ ID NO 36
<211> LENGTH: 21
<212> TYPE: DNA
<213> ORGANISM: Artificial Sequence
<220> FEATURE:
<223> OTHER INFORMATION: PCR Primer

<400> SEQUENCE: 36
gccgggtttg agttagcaga t                                           21
```